United States Patent [19]

Farooq

[11] Patent Number: 4,897,485
[45] Date of Patent: Jan. 30, 1990

[54] INSECTICIDAL PYRID-3-YL-2,3-DIAZA-BUTADIEN-1-YL-DISULFIES

[75] Inventor: Saleem Farooq, Arisdorf, Switzerland

[73] Assignee: Ciba-Geigy Corporation, Ardsley, N.Y.

[21] Appl. No.: 166,945

[22] Filed: Mar. 11, 1988

[30] Foreign Application Priority Data

Mar. 18, 1987 [CH] Switzerland ............ 1028/87
Apr. 9, 1987 [CH] Switzerland ............ 1361/87

[51] Int. Cl.$^4$ ............ A61K 31/44; C07D 211/80; C07D 401/02; C07D 401/14
[52] U.S. Cl. ............ 546/264; 534/751; 546/277; 546/330; 546/331; 546/332
[58] Field of Search ............ 546/331, 332, 330, 264

[56] References Cited

U.S. PATENT DOCUMENTS

| | | | |
|---|---|---|---|
| 2,719,161 | 9/1955 | Behnisch et al. | 546/331 |
| 2,729,644 | 1/1956 | Klopping | 546/331 |
| 3,668,076 | 6/1972 | Rey et al. | 546/332 X |
| 4,233,302 | 11/1980 | Martin-Smith et al. | 546/332 X |
| 4,699,913 | 10/1987 | Farooq et al. | 514/333 |

OTHER PUBLICATIONS

Synthesis, No. 11, pp. 561–580 (1970), Kuhle.
J. Chem. Soc., Chem. Commun., (1982), pp. 188–189, Evans et al.
Khimiya Geterotsiklicheskikh Soedinenii, No. 7, pp. 904–910 (1982), (Translated) Zelenin et al.

*Primary Examiner*—Floyd D. Higel
*Attorney, Agent, or Firm*—Kevin T. Mansfield; Edward McC. Roberts

[57] ABSTRACT

Pyrid-3-yl-2,3-diazabutadiene-1-yl]-disulfides of formula

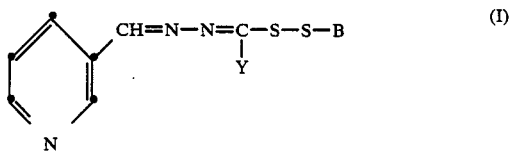

wherein
  B is unsubstituted or substituted $C_1$-$C_6$ alkyl, phenyl or substituted phenyl, or is the radical 0011 and
  Y is an unsubstitued or a substituted aromatic carbocycle or heterocycle,
  and the salts and optical isomers thereof, processes for the preparation of these compounds and compositions containing them for use in pest control, especially for controlling insects that attack plants and animals. The compounds are particularly effective against plant-destructive sucking insects.

10 Claims, No Drawings

INSECTICIDAL PYRID-3-YL-2,3-DIAZA-BUTADIEN-1-YL-DISULFIES

The present invention relates to novel insecticidal pyridyldiazabutadienyl disulfides, to their preparation, to compositions which contain these compounds and to the use thereof in pest control.

The pyridyldiazabutadienyl disulfides of this invention, and the salts thereof, have the formula I

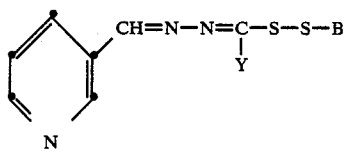   (I)

wherein

B is unsubstituted or substituted $C_1$–$C_6$alkyl, phenyl or subtituted phenyl, or is the radical

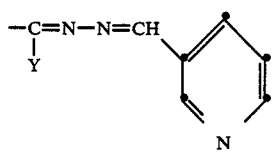

and

Y is an unsubstituted or a substituted aromatic carbocycle or heterocycle.

Preferred compounds of this invention are those of formula Ia

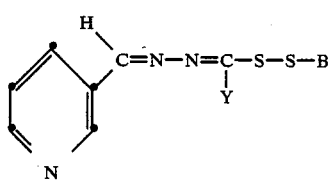

wherein

Y is an unsubstituted or a substituted aromatic carbocycle or heterocycle, and

B is unsubstituted or substituted $C_1$–$C_6$alkyl or phenyl or substituted phenyl.

On account of their insecticidal activity, those compounds of formula Ia are preferred wherein Y is pyridyl, phenyl or substituted phenyl, B is $C_1$–$C_6$alkyl, $C_1$–$C_6$-alkyl which is substituted by one or more halogen atoms, $C_1$–$C_4$alkoxy-$C_1$–$C_6$alkyl, $C_1$–$C_4$alkylthio-$C_1$–$C_6$alkyl, $C_1$–$C_6$cyanoalkyl, $C_1$–$C_4$nitroalkyl, or is the radical

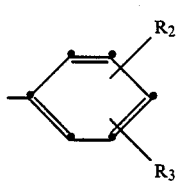

wherein $R_2$ and $R_3$ are each independently of the other hydrogen, halogen, $C_1$–$C_4$alkyl, trifluoromethyl, $C_1$–$C_4$alkoxy or nitro.

Among this group of compounds, those compounds are preferred in which Y is pyridyl or the radical

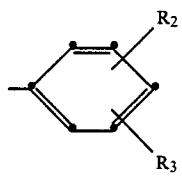

wherein $R_2$ and $R_3$ are each independently of the other hydrogen, halogen, $C_1$–$C_4$alkyl, trifluoromethyl, $C_1$–$C_4$alkoxy or nitro, and B is $C_1$–$C_4$cyanoalkyl.

A particularly preferred compound is [1-(4-chlorophenyl)-4-(pyrid-3-yl)-2,3-diazabutadien-1-yl]-(1,1-dimethyl-1-cyanomethyl) disulfide.

Further preferred compounds of formula Ia are those wherein Y is pyridyl or the radical

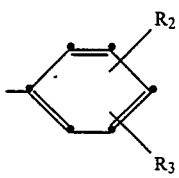

wherein $R_2$ and $R_3$ are each independently of the other hydrogen, halogen, $C_1$–$C_4$alkyl, trifluoromethyl, $C_1$–$C_4$alkoxy or nitro, and B is phenyl, nitrophenyl, 4-chlorophenyl or 4-tolyl.

Among this group of compounds, those compounds are particularly preferred wherein Y is 4-chlorophenyl.

Preferred compounds of this invention are also those of formula Ib

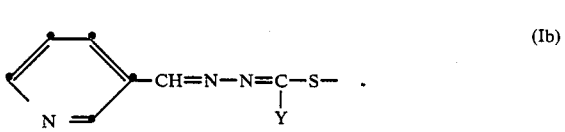   (Ib)

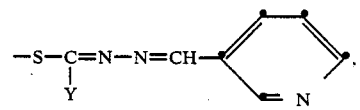

wherein Y is a radical

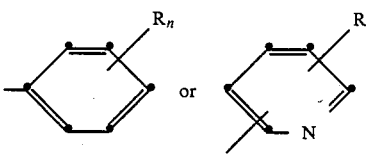

wherein

R is hydrogen, $C_1$–$C_4$alkyl, halogen, nitro, cyano, $C_1$–$C_4$alkoxy, $C_1$–$C_4$alkylthio, $C_1$–$C_4$haloalkyl containing 1 to 9 halogen atoms, $C_1$–$C_4$haloalkoxy containing 1 to 9 halogen atoms, $C_1$–$C_4$haloalkylthio containing 1 to 9 carbon atoms, phenyl-substituted phenyl, phenylalkyl containing 1 to 3 carbon atoms in the alkyl moiety, phenoxy, phenylthio or pyridyloxy, and n is an integer from 1 to 5, and the salts thereof.

Preferred compounds of formula Ib are those wherein R is hydrogen, $C_1$-$C_4$alkyl, halogen, nitro, cyano, $C_1$-$C_4$alkoxy, $C_1$-$C_4$alkylthio, $C_1$-$C_4$haloalkyl containing 1 to 9 carbon atoms, $C_1$-$C_4$haloalkoxy containing 1 to 9 halogen atoms or $C_1$-$C_4$haloalkylthio containing 1 to 9 halogen atoms, and n is 1 to 3.

Further preferred compounds of formula Ib are those wherein R is hydrogen, $C_1$-$C_4$alkyl, fluorine, chlorine, bromine, nitro, $C_1$-$C_4$alkoxy or trifluoromethyl.

Particularly preferred compounds of formula Ib are those wherein n is 1 or 2 and those wherein Y is the radical

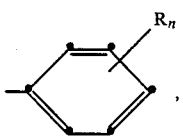

wherein at least one substituent R is in 4-position.

Within the scope of this invention, alkyl by itself or as moiety of another substituent will be understood as meaning straight chain or branched alkyl radicals and, depending on the indicated number of carbon atoms, e.g. the following groups: methyl, ethyl, propyl, butyl, as well as the isomers thereof, e.g. isopropyl, isobutyl, tert-butyl, sec-butyl and the like.

The term "haloalkyl" will be understood as meaning within the scope of this invention straight chain and branched alkyl radicals such as methyl, ethyl, n-propyl, isopropyl, butyl and the like, which radicals are substituted by up to 9 different or identical halogen atoms. These radicals may be perhalogenated alkyl radicals or also those in which only some of the hydrogen atoms are substituted by halogen.

Halogen will be understood as meaning fluorine, chlorine, bromine and iodine, with fluorine and chlorine being preferred.

The carbocyclic or heterocyclic aryl radicals within the scope of this invention are unsubstituted or substituted phenyl, 1- or 2-naphthyl and pyridyl.

The present invention also relates to the salts, in particular the phytophysiologically acceptable salts, of the compounds of formula I. Examples of such salts with organic and inorganic acids are: chlorides, bromides, iodides, sulfates, bisulfates, chlorates, perchlorates, rhodanides, nitrates, phosphates, hydrogen phosphates, tetrafluoroborates, formates, acetates, trichloroacetates, trifluoroacetates, phenylsulfonates, oxalates, malonates, succinates, malates, tartrates or citrates.

The compounds of formula Ia can be prepared by reacting a 5-pyridyl-4,5-dihydrothiadiazole of formula II

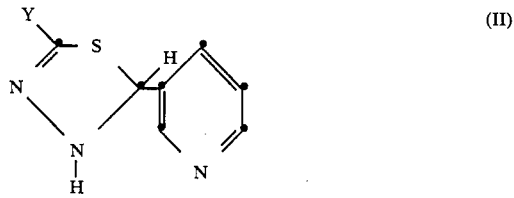

first with a base and then with a sulfenyl chloride of formula III $$Cl-S-B \quad (III),$$

in which formulae (II) and (III) above Y and B are as previously defined, and, if desired, converting the product into a salt thereof and isolating said salt.

This process is novel and likewise constitutes an object of the invention.

The sulfenyl chlorides of formula III are known, commercially available compounds and their preparation by known methods is disclosed in the literature. An overview of the preparatory methods of obtaining the sulfenyl chlorides has been published in "Synthesis", 561-580 (1970).

In the process of this invention for the preparation of the pyridyldiazabutadienyl sulfides of formula Ia, the dihydrothiadiazole of formula II can be reacted with an inorganic base such as potassium or sodium hydroxide or potassium or sodium hydroxide, as well as with an organic base such as a trialkylamine.

The process for the preparation of compounds of formula Ia is preferably carried out in a solvent. Examples of suitable solvents are aromatic hydrocarbons such as benzene, toluene and xylene; ketones such as acetone, cyclohexanone and methyl ether ketone; ethers such as tetrahydrofuran, dioxane and diethyl ether; halogenated hydrocarbons such as chloroform, carbon tetrachloride and chlorobenzene; alcohols such as ethanol and propanol; esters of aliphatic acids such as ethyl acetate; aliphatic amides such as dimethylformamide and dimethylacetamide; dimethyl sulfoxide and other solvents which do not impair the reaction. Mixtures of these solvents may also be employed. The reaction temperatures may be in a wide range from $-10°$ to $+200°$ C. A temperature range from room temperature to about 150° C. is preferred.

The compounds of formula Ib can be prepared by oxidising a compound of formula II, preferably in the presence of a base. Examples of suitable oxidising agents are chlorine, iodine or oxygen. Examples of bases which may be suitably used for the process are hydroxides or carbonates of alkali metals or alkaline earth metals such as KOH, NaOH, $K_2CO_3$, $Na_2CO_3$ and the like.

The process for the preparation of the compounds of formula Ib is also preferably carried out in a solvent. The reaction temperature may vary within a wide range from $-10°$ to $+100°$ C. A preferred temperature range is from about 0° to 60° C.

Suitable solvents for the preparation of compounds of formula I are aromatic hydrocarbons such as benzene, toluene and xylene; ketones such as acetone, cyclohexanone and methyl ethyl ketone; ethers such as tetrahydrofuran, dioxane and diethyl ether; halogenated hydrocarbons such as chloroform, carbon tetrachloride and chlorobenzene; alcohols such as ethanol and propanol; esters of aliphatic acids auch as ethyl acetate; aliphatic amides such as dimethylformamide and dimethylacetamide; dimethyl sulfoxide and other solvents which do not impair the reaction. Mixtures of these solvents may also be employed.

The starting compounds of formula II can be prepared in a manner known per se (q.v. D. M. Evans et al., J. Chem. Soc., Chem. Commun. 1982, p. 188; K. N. Zelenin et al., Khim. Geterotsikl. Soedin, 1982 (No. 7), p. 904) by reacting a compound of formula IV

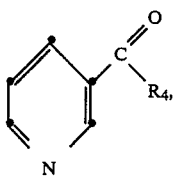

with a compound of formula V

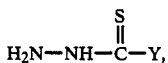

in which compounds of formulae IV and V above R₄ and n are as defined above for formula Ib.

The compounds of formula II can also be prepared according to European patent application 0 207 004 by reacting a compound of formula VI

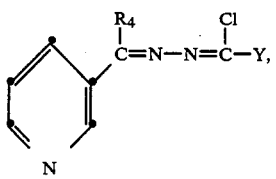

wherein R₄ and n have the meanings given above, with a sulfide.

Surprisingly, it has been found that the compounds of formula I have excellent activity as pesticides, while being well tolerated by plants and having low mammalian toxicity to warm-blooded animals. The compounds of formula I are particularly suitable for controlling pests that attack plants and animals.

In particular, the compounds of formulae I and Ia are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina.

The good pesticidal activity of the compounds of the invention corresponds to a mortality of at least 50–60% of the above pests.

Most particularly, plant-destructive insects, especially plant-destructive insects in ornamentals and crops of useful plants, in particular in cotton, vegetable, rice and fruit crops, can be controlled with the compounds of formula I. In this connection, particular attention is drawn to the fact that the compounds of formula I have a strongly pronounced systemic as well as contact action against sucking insects, especially against insects of the Aphididae family (e.g. against Aphis fabae, Aphis craccivora and Myzus persicae) which can only be controlled with difficulty using known pesticides.

The compounds of formula I also exhibit good activity against larval insect stages and nymphs, especially of noxious feeding insects. In particular, the compounds of formula 1 can be used with great success against plant-destructive cicadas, especially in rice crops.

The compounds of formula I are also suitable for controlling ectoparasites, e.g. Lucilia sericata, and ticks on domestic animals and productive livestock, e.g. by treating animals, barns, stables and pastures.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenyl with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alklypolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acids esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients for obtaining special effects.

EXAMPLE 1

Preparation of starting compounds (a) Preparation of 2-(4-chlorophenyl)-5-(pyrid-3-yl)-4,5-dihydro-1,3,4-thiadiazole 39.2 g of p-chlorothiobenzhydrazide are dissolved in 350 ml of ethanol. A solution of 21.4 g of pyrid-3-aldehyde in 20 ml of ethanol is added dropwise, under nitrogen, to the above solution. The reaction temperature is kept at 20° C. by cooling. When the addition is complete, the reaction mixture is stirred for 1 hour at reflux temperature and thereafter filtered through finely particulate diatomaceous earth. The filtrate is concentrated to three-quarters of its initial volume and the precipitated product is isolated by filtration, washed with hexane and dried, affording the title compound of formula

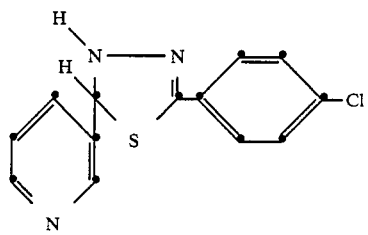

with a melting point of 106°–108° C.

(b) Preparation of 2-(3-nitrophenyl)-5-(pyrid-3-yl)-4,5-dihydro-1,3,5-thiadiazole A solution of 8.7 g of potassium hydroxide in 100 ml of ethanol is saturated with hydrogen sulfide. Then 8.7 g of potassium hydroxide in 100 ml of ethanol are added dropwise to this solution. While cooling with ice, 22.4 g of 1-chloro-1-(3-nitrophenyl)-4-(3-pyridyl)-3-diazabutadiene are added, in portions, to the resultant solution. The reaction mixture is thereaftr stirred for 1 hour at room temperature, then concentrated, and the residue is taken up in ethyl acetate. The ethyl acetate solution is washed twice with water and twice with a saturated solution of sodium chloride, dried over sodium sulfate and filtered. Concentration of the filtrate yields the title compound of formula

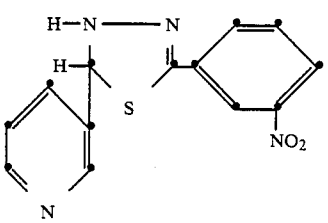

with a melting point of 109°–111° C.

EXAMPLE 2

Preparation of 1-(4-chlorophenyl)-4-(pyrid-3-yl)-2,3-diazabutadien-1-yl-1,1-dimethyl-1-cyanomethyl disulfide To a solution of 13.8 g (0.05 mol) of 2-(4-chlorophenyl)-5-(pyrid-3-yl)-4,5-dihydrothiazole (EP-A 207 004) in 80 ml of tetrahydrofuran are added 6.1 g (0.06 mol) of triethylamine and the solution is cooled to 0°–5° C. A solution of 6.8 g (0.05 mol) of α-(chlorothio)isobutyronitrile in 10 ml of tetrahydrofuran is then added dropwise to the above solution over 10 minutes. The reaction mixture is stirred for 5 hours at 20°–25° C., filtered, and the mother liquor is concentrated by evaporation at 60° C. under vacuum. The residue is dissolved in 200 ml of ethyl acetate and the ethyl acetate solution is washed with 20 ml of water and 20 ml of a saturated solution of sodium chloride, dried over sodium sulfate and filtered. The filtrate is concentrated by evaporation at 60° C. under vacuum and the crude product obtained as residue is dissolved in ethyl acetate. The cold solution is filtered over silica gel and the solvent is removed by evaporation.

The residue consists of the desired 1-(4-chlorophenyl)-4-(pyrid-3-yl)-2,3-diazabutadien-1-yl-1,1-dimethyl-1-cyanomethyl disulfide in purified form having a melting point of 83°–85°:

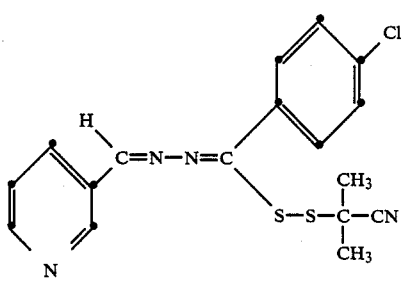

The following compounds of formula Ia are prepared in analogous manner:

TABLE 1

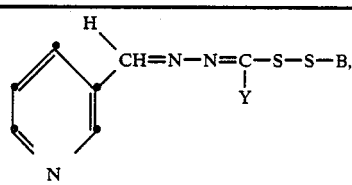

(Ia)

| Compound | Y | B | physical data |
|---|---|---|---|
| 1 | 4-Cl—$C_6H_4$— | —$C(CH_3)_2CN$ | m.p. 83–85° C. |
| 2 | 4-$CH_3$—$C_6H_4$— | —$C(CH_3)_2CN$ | m.p. 78–79° C. |
| 3 | 4-$CF_3$—$C_6H_4$— | —$C(CH_3)_2CN$ | m.p. 82–84° C. |
| 4 | 4-$CH_3O$—$C_6H_4$— | —$C(CH_3)_2CN$ | $n_D^{20}$: 1.6569 |
| 5 | 4-F—$C_6H_4$— | —$C(CH_3)_2CN$ | m.p. 97–98° C. |
| 6 | 4-Br—$C_6H_4$— | —$C(CH_3)_2CN$ | $n_D^{20}$: 1.6608 |
| 7 | 3-$CH_3$—$C_6H_4$— | —$C(CH_3)_2CN$ | |
| 8 | 3-$CF_3$—$C_6H_4$— | —$C(CH_3)_2CN$ | $n_D^{20}$: 1.5964 |
| 9 | 3-Cl—$C_6H_4$— | —$C(CH_3)_2CN$ | m.p. 66–68° C. |
| 10 | 3,4-$Cl_2$—$C_6H_3$ | —$C(CH_3)_2CN$ | |
| 11 | 2,4-$Cl_2$—$C_6H_3$— | —$C(CH_3)_2CN$ | m.p. 126–128° C. |
| 12 | 3-pyridyl- | —$C(CH_3)_2CN$ | m.p. 92–94° C. |
| 13 | 2-pyridyl- | —$C(CH_3)_2CN$ | |
| 14 | 4-pyridyl- | —$C(CH_3)_2CN$ | |
| 15 | 4-Cl—$C_6H_4$— | 4-$NO_2$—$C_6H_4$— | |
| 16 | 4-Cl—$C_6H_4$— | 3-$NO_2$—$C_6H_4$— | |
| 17 | 4-Cl—$C_6H_4$— | 2-$NO_2$—$C_6H_4$— | |
| 18 | 4-Cl—$C_6H_4$— | $C_6H_5$— | |
| 19 | 4-Cl—$C_6H_4$— | 4-Cl—$C_6H_4$— | |
| 20 | 4-Cl—$C_6H_4$— | 4-$CH_3$—$C_6H_4$— | m.p. 104–106° C. |

EXAMPLE 3

Preparation of bis[1-(4-chlorophenyl)-4-(pyrid-3-yl)2,3-diazabutadien-1-yl]disulfide 3.6 g of powdered potassium hydroxide are added to a solution, cooled to 0° C., of 15 g of the 2-(4-chlorophenyl)-5-(pyrid-3-yl)-4,5-dihydro-1,3,4-thiadiazole prepared according to Example 1a) in 80 ml of acetone. After stirring for ca. 5 minutes at 0°–5° C., 6.9 g of iodine are added in portions and the exothermic reaction is kept at about 0°–5° C. by cooling with ice. The batch is subsequently stirred for 4 hours at ca. 0° C. The precipitated product is isolated by filtration and washed with a small amount of acetone. The crude product is taken up in a 1:3 mixture of tetrahyrofuran/ethyl acetate and the solution is washed once with water and twice with a saturated solution of sodium chloride, dried over sodium sulfate and concentrated by evaporation. The title compound of formula

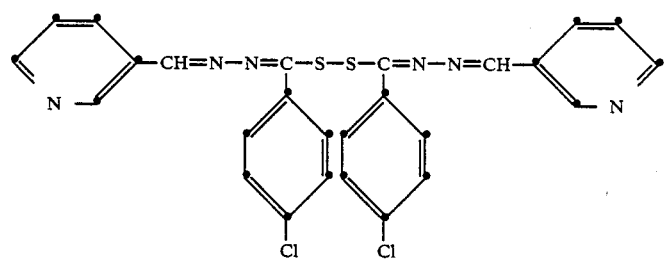

so obtained has a melting point of 143°–145° C. (compound 21).

The following compound:

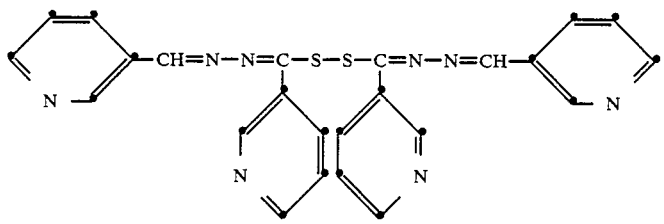

is also obtainable in a manner similar to that described above. Melting point: 105°–108° C. (compound 22).

The following compounds of formula Ib, wherein Y has the indicated meanings, can also be obtained as described above:

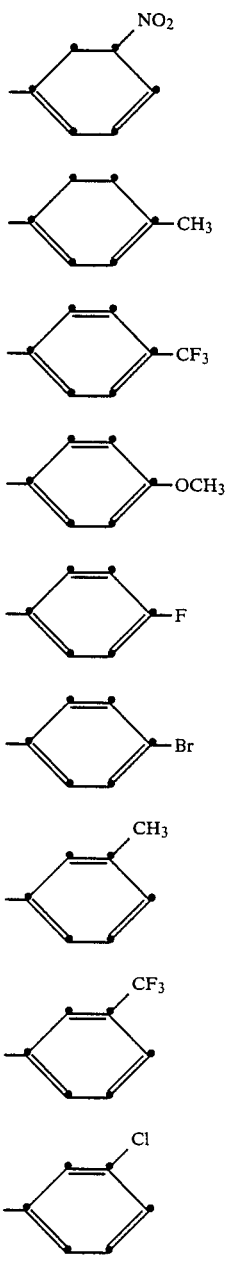

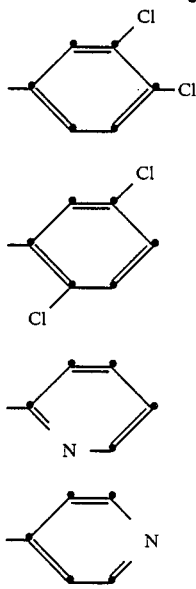

EXAMPLE 4

Formulations for compounds of formula I according to Examples 2 and 3 or combinations thereof with other insecticides or acaricides (throughout, percentages are by weight)

| 1. Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| compound of formula I or combination | 10% |
| octylphenol polyethylene glycol ether (4–5 mol of ethylene oxide) | 3% |
| calcium dodecylbenzenesulfonate | 3% |
| castor oil polygycol ether (36 mol of ethylene oxide) | 4% |
| cyclohexanone | 30% |

-continued

| 2. Emulsifiable concentrate | |
|---|---|
| xylene mixture | 50% |

Emulsions of any required concentration can be obtained from this concentrate by dilution with water.

| 3. Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carrier, and grinding the mixture in a suitable mill.

| 4. Extruder granulate | |
|---|---|
| compound of formula I or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| 5. Coated granulate | |
|---|---|
| compound of formula I or combination | 3% |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| compound of formula I or combination | 40% |
| ethyleno glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8 |
| water | 32% |

The finely ground active ingredient or combination is intimately mixed with the adjuvants, giving a suspension concentrate from which suspensions of any desired concentration can be obtained by dilution with water.

BIOLOGICAL EXAMPLES

EXAMPLE 5.1

Action against *Musca domestica*

50 g of freshly prepared CMSA nutrient substrate for maggots are charged into each of a number of beakers. A specific amount of an acetonic solution containing 1% by weight of the respective test compound is pipetted onto the nutrient substrate present in the beakers to given an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with the test compound at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formula I according to Examles 2 and 3 are very effective in this test.

EXAMPLE 5.2

Action against *Lucilia sericata*

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

Compounds of formula I according to Examples 2 and 3 are very effective against *Lucilia sericata* in this test.

EXAMPLE 5.3

Action against *Aëdes aegypti*

A concentration of 200 ppm is obtained by pipetting a specific amount of a 0.1% solution of the test compound in acetone onto the surface of 150 ml of water in a beaker. After the acetone has evaporated, 30 to 40 two-day-old larvae of *Aëdes aegypti* are put into the beaker containing the test compound. Mortality counts are made after 2 and 7 days.

Compounds of formula I according to Examples 2 and 3 are very effective in this test.

EXAMPLE 5.4

Contact action against *Aphis craccivora*

Before the start of the test, 4- to 5-day old bean seedlings (*Vicia faba*) reared in pots are each populated with about 200 insects of the species *Aphis craccivora*. The treated plants are sprayed direct to drip point 24 hours later with an aqueous formulation containing the test compound. Two plants are used for each test compound at its given concentration. A mortality count is made after 24 and 72 hours respectively. The test is carried out at 21°-22° C. and at a relative humidity of about 55%.

In this test, compound 1 of Example 2 effects 80 to 100% kill at a concentration of 400 ppm.

The compounds of formula V according to Example 3 are also very effective in this test.

EXAMPLE 5.5

Systemic action against *Aphis craccivora* (soil)

Bean plants which have grown roots are transplanted into pots containing 600 ccm of soil. Then 50 ml of a formulation (prepared from a 25% wettable powder) of the test compound in a concentration of 800 ppm are poured direct onto the soil in the pots.

After 24 hours the growing parts of the plants are populated with aphids of the species *Aphis craccivora* and a plastic cylinder is then slipped over the plants to protect the aphids from any possible contact with the test substance either direct or via the gas phase.

A mortality count is made 48 and 72 hours respectively after the start of the test. Two plants, each in a separate pot, are used for each test compound at its given concentration. The test is carried out at 25° C. and about 70% relative humidity. Compounds of formula I according to Examples 2 and 3 exhibit good activity in this test.

EXAMPLE 5.6

Contact action against *Myzus persicae*

4- to 5-day old bean plants (*Vicia faba*) which have been reared in water are each populated with about 200 aphids of the species *Myzus persicae* before the start of the test. The treated plants are sprayed direct to drip point 24 hours later with an aqueous suspension containing the test compound in a concentration of up to 200 ppm. Two plants are used for each compound at its given concentration. An evaluation of percentage mortality is made 24 and 72 hours respectively after application. The test is carried out at 20°–22° C. and about 60% relative humidity.

In this test, 80 to 100% kill is effected by compound 1 according to Example 2 at 12.5 ppm and by compound 21 according to Example 3 at 12.5 ppm.

EXAMPLE 5.7

Systemic action against *Myzus persicae*

Cabbage plants which have grown roots are transplanted in the 4- to 5-leaf stage into pots containing 60 ccm of soil. Then 50 ml of an aqueous formulation (prepared from a 25% wettable powder) of the test compound in a concentration of 800 ppm are poured direct onto the soil.

After 24 hours the parts of the plants above the soil are populated with aphids of the species *Myzus persicae* and plastic cylinders are then slipped over the plants to protect the aphids from any possible contact with the test substance either direct or via the gas phase.

The evaluation of percentage mortality is made 48 hours after the start of the test. Two plants, each in a separate pot, are used for each test substance at its given concentration. The test is carried out at about 25° C. and 60% relative humidity.

Compounds of formula I according to Examples 2 and 3 exhibit good activity in this test.

EXAMPLE 5.8

Leaf penetration action against *Aphis craccivora*

A small shoot of *Vicia faba*, which is heavily infested with aphids of the species *Aphis craccivora*, is placed in each of a number of 8 cm higher plastic beakers (diameter about 6 cm). Each beaker is covered with a cardboard lid having a punched opening of 2.5 cm diameter in the centre. A leaf of a *Vicia faba*-plant is then placed over the opening in the lid without separating this leaf from the potted plant. The leaf is then fixed on the beaker with a second punched cardboard lid above the opening of the first lid. From underneath, i.e. through the opening of the first lid, the aphids in the beaker then infect the leaf of the plant used as bait. An aqueous formulation of the test compound is then applied in a concentration of 400 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

Compounds of formula I according to Examples 2 and 3 are very effective in this test.

EXAMPLE 5.9

Stomach toxicant action against *Laodelphax striatellus* and *Nilaparvata lugens* (nymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an acetonic solution containing 400 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

Compounds of formula I according to Examples 2 and 3 are very effective in this test.

EXAMPLE 5.10

Ovicidal action against *Laodelphax striatellus* and *Nilaparvata lugens*

The test is carried out with growing plants. For this purpose 4 rice plants (thickness of stem 8 mm; height about 20 cm) are planted into each of a number of pots (diameter 8 cm).

The plants in each pot are sprayed on a rotary table with 100 ml of an acetonic solution containing 400 ppm of the respective test compound. After the spray coating has dried, each plant is populated with 3 adult females. To prevent the females from escaping, a glass cylinder is slipped over each of the plants and sealed with a gauze top. The females are left on the treated plant for 4 days for oviposition and are then removed.

About 8 days after the females have been placed on the plants, the young cicadas hatch from the eggs and a count is made. The percentage mortality is calculated by comparing the number of larvae which have hatched on the treated plants with the number which have hatched on the untreated control plants.

Compounds of formula I according to Examples 2 and 3 are very effective in this test.

What is claimed is:

1. A compound of formula I

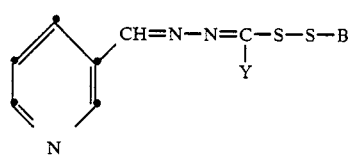

wherein
Y is pyridyl or the radical

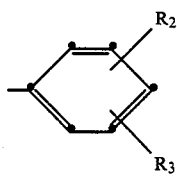

wherein $R_2$ and $R_3$ are each independently of the other hydrogen, halogen, $C_1-C_4$alkyl, trifluoromethyl, $C_1-C_4$alkoxy or nitro and B is $C_1-C_6$alkyl, $C_1-C_6$alkyl which is substituted by halogen, $C_1-C_4$alkoxy-$C_1-C_6$alkyl, $C_1-C_4$alkylthio-$C_1-C_6$alkyl, $C_1-C_6$cyanoalkyl, $C_1-C_4$nitroalkyl, or is the radical

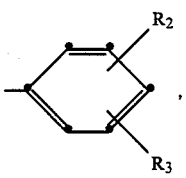

wherein $R_2$ and $R_3$ are each independently of the other hydrogen, halogen, $C_1-C_4$alkyl, trifluoromethyl, $C_1-C_4$alkoxy or nitro, or is the radical

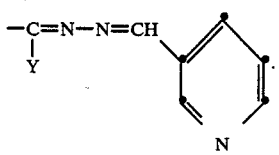

2. A compound according to claim 1, wherein Y is pyridyl or the radical

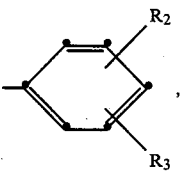

wherein $R_2$ and $R_3$ are each independently of the other hydrogen, halogen, $C_1-C_4$alkyl, trifluoromethyl, $C_1-C_4$alkoxy or nitro, and B is $C_1-C_4$cyanoalkyl.

3. [1-(4-Chlorophenyl)-4-(pyrid-3-yl)-2,3-diazabutadien-1-yl]-(1,1-dimethyl-1-cyanomethyl)disulfide according to claim 2.

4. A compound according to claim 1, wherein Y is pyridyl or the radical

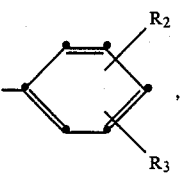

wherein $R_2$ and $R_3$ are each independently of the other hydrogen, halogen, $C_1-C_4$alkyl, trifluoromethyl, $C_1-C_4$alkoxy or nitro, and B is phenyl, nitrophenyl, 4-chlorophenyl or 4-tolyl.

5. A compound according to claim 4, wherein Y is 4-chlorophenyl.

6. A compound of formula Ib according to claim 1

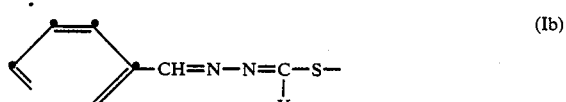   (Ib)

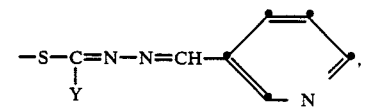

wherein Y is a radical

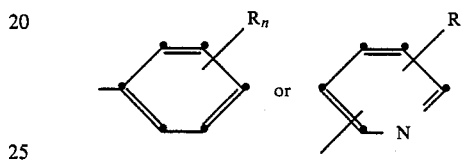

wherein
R is hydrogen or halogen, and
n is 1.

7. A compound according to claim 6, wherein R is hydrogen, fluorine, chlorine or bromine.

8. A compound according to claim 6, wherein Y is the radical

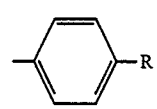

9. A compound according to claim 8 of formula

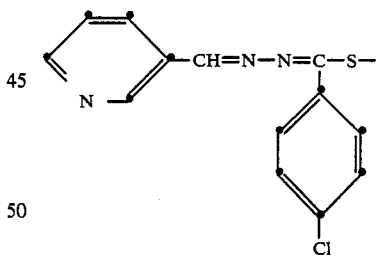

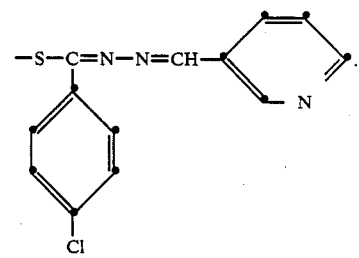

10. A pesticidal composition which comprises, as active component, a pesticidally active amount of a compound as claimed in claim 1 together with a pesticidally acceptable carrier or other inert adjuvant.

* * * * *